US005368817A

United States Patent [19]

Sudo et al.

[11] Patent Number: 5,368,817

[45] Date of Patent: Nov. 29, 1994

[54] DAMPENING WATER CONTROLLER

[75] Inventors: Toru Sudo; Takashi Kuramoto; Yasuhiro Seno; Masao Mogi; Hisato Urase, all of Tokyo, Japan

[73] Assignee: Toppan Printing, Co., Ltd., Tokyo, Japan

[21] Appl. No.: 85,158

[22] Filed: Jul. 2, 1993

[30] Foreign Application Priority Data

| | | | |
|---|---|---|---|
| Jul. 8, 1992 | [JP] | Japan | 4-180835 |
| Oct. 7, 1992 | [JP] | Japan | 4-268451 |
| Mar. 25, 1993 | [JP] | Japan | 5-066803 |

[51] Int. Cl.[5] .......... G01N 33/00; B41F 33/00

[52] U.S. Cl. .......... 422/62; 422/68.1; 422/82.01; 422/82.03; 422/105; 422/108; 436/50; 436/55; 436/147; 436/149; 436/150; 101/148

[58] Field of Search .......... 422/62, 68.1, 82.01, 422/82.02, 82.03, 105, 108; 436/50, 55, 147, 149, 150; 101/148

[56] References Cited

U.S. PATENT DOCUMENTS

| | | | |
|---|---|---|---|
| 4,388,864 | 6/1983 | Warner | 101/148 |
| 4,668,346 | 5/1987 | Entwistle | 422/82.03 |
| 4,814,281 | 3/1989 | Byers | 436/150 |
| 4,911,891 | 3/1990 | Platt | 422/68.1 |
| 5,102,520 | 4/1992 | Behr et al. | 204/129.65 |
| 5,181,467 | 1/1993 | Takekoshi | 101/147 |

FOREIGN PATENT DOCUMENTS

| | | |
|---|---|---|
| 0170160 | 2/1986 | European Pat. Off. . |
| 0227949 | 7/1987 | European Pat. Off. . |
| 0378497 | 7/1990 | European Pat. Off. . |
| 3822344 | 1/1990 | Germany . |
| 2206413 | 1/1989 | United Kingdom . |

*Primary Examiner*—James C. Housel
*Assistant Examiner*—Long V. Le
*Attorney, Agent, or Firm*—Armstrong, Westerman, Hattori, McLeland & Naughton

[57] ABSTRACT

A dampening water controller for controlling the concentration of an etching solution in dampening water circulatively used in offset printing, includes an ion concentration measuring means capable of measuring the concentration of at least one kind of ion (object ions) selected from specific anions or cations contained only in an etching solution in dampening water. Information on the measured concentration of the ions in the dampening water is output. A dampening water temperature measuring device capable of measuring the temperature of the dampening water and outputting information on the measured temperatures is provided. Also, an ion concentration information correcting device is provided capable of correcting the information on the measured concentration of the ions in the dampening water, in accordance with the information on the measured temperature of the dampening water. The controller also includes an etching solution concentration adjusting device capable of adjusting the concentration of the etching solution in the dampening water, in accordance with the corrected information on the ion concentration.

15 Claims, 9 Drawing Sheets

DAMPENING WATER CONTROLLER

BACKGROUND OF THE INVENTION

1. Field of the Invention

This invention relates to an apparatus for controlling dampening water circulatively used in offset printers. More particularly, it is concerned with an improvement in a dampening water controller or controlling apparatus for controlling the concentration of etching solution in dampening water containing an alcohol or surface active agent and an etching solution as well as impurities such as ink and paper dust that can be brought into the dampening water as it is used circulatively.

2. Description of the Prior Art

In offset printing, what is called dampening water is usually made to adhere to non-image areas on which no ink must be laid, to cause that areas to repel ink so that the ink can be controlled to adhere or not to adhere according to a pattern on a plate. Accordingly, how the dampening water is maintained and controlled to function at a high performance is a very important subject for the quality of prints obtained by offset printing. Now, the dampening water usually contains water, an etching solution (a solution added to dampening water when used) and an alcohol such as isopropyl alcohol or ethyl alcohol or a surface active agent.

The alcohol or surface active agent, though contained in a trace amount, decreases the surface tension of the dampening water to thereby improve its wettability to a plate and so functions as to uniformly spread the dampening water over the whole plate. That is, the alcohol or surface active agent contained in an appropriate amount greatly contributes a fundamental performance of the offset printing.

The etching solution also contains gum arabic, which is a colloidal substance comprised of a water-soluble polymer. The gum arabic has what is called a desensitizing action. This desensitizing action is greatly affected by pH values, and is considered to exhibit its highest function in a certain specific pH range. For this reason, anions such as nitrate ions, nitrite ions, phosphate ions, fluoride ions, chloride ions, sulfate ions or sulfide ions or cations such as sodium ions, ammonium ions, calcium ions or potassium ions are usually mixed in the etching solution. Using these various kinds of ions and a pH adjuster optionally added, the pH value of the dampening water containing the etching solution is adjusted so as to be set in a specific pH range, usually in a pH range of from 4.0 to 6.5.

As apparatus for controlling this dampening water, a system has been hitherto employed in which the pH and alcohol concentration of dampening water being used are monitored and the concentration of etching solution and concentration of alcohol in the dampening water are controlled in accordance with the resulting data.

Incidentally, when the dampening water is circulatively used (which is commonly circulated for the purpose of, e.g., saving the dampening water.), impurities such as ink and paper dust are usually brought into the dampening water that has returned without being consumed on a printer. Now, the paper commonly contains calcium carbonate as its component, and hence the pH value of the dampening water tends to become higher with an increase in the quantity of calcium carbonate in the dampening water. For this reason, the control made in accordance with pH values of the dampening water has been disadvantageous in that the presence of calcium carbonate makes it difficult to accurately judge the concentration of etching solution in the dampening water. Namely, what is important as characteristic values for controlling the dampening water is not the pH values but the etching solution concentration itself in the dampening water.

Under such circumstances, as disclosed, for example, in Japanese Patent Application Laid-open No. 56-157360 or No. 63-1543, it is attempted to monitor conductivity of dampening water being used and control the concentration of etching solution in accordance with the resulting data. This method, though it is based on not the controlling of the etching solution concentration itself but the idea that the conductivity is proportional to the concentration of etching solution, has an advantage that the measurement itself is very easy.

However, according to this method, a conductivity of the dampening water having returned from a water fountain (a long and slender pad containing dampening water, which is provided in the circulation path of dampening water and through which the dampening water is fed to the surface of a plate) is measured. Hence, when the above impurities have been brought into the dampening water as a result of its circulative use, the impurities may affect the dampening water to change its conductivity, resulting in a break of the relationship between the concentration of etching solution in the dampening water and the conductivity of the dampening water. Thus, there has been the problem that the concentration of etching solution in the dampening water can be misjudged.

Here, the concentration (%) of etching solution in the dampening water is defined as:

$$100Y/(X+Y+Z)\ (\%)$$

wherein X represents a quantity of water before the mixing of a stock solution of the etching solution, Y represents a quantity of a stock solution of the etching solution, and Z represents a quantity of an alcohol.

With regard to the concentration (%) of alcohol in the dampening water, it is defined as follows:

$$100Z/(X+Y+Z)\ (\%)$$

SUMMARY OF THE INVENTION

The present invention was made taking note of the problems discussed above. An object thereof is to provide a dampening water controller that can control the concentration of etching solution in dampening water in a high precision and can maintain the concentration of etching solution in dampening water at a proper degree.

Another object of the present invention is to provide a dampening water controller that can control the concentration of etching solution in dampening water in a high precision and also can perform maintenance of the apparatus with ease.

The present invention provides a dampening water controller for controlling the concentration of an etching solution in dampening water circulatively used in offset printing, comprising;

an ion concentration measuring means capable of measuring the concentration of anions or cations contained in the etching solution in said dampening water; said anions being selected from the group consisting of nitrate ions, nitrite ions, phosphate ions, fluoride ions, sulfate ions and sulfide ions and said cations being selected from the group consisting of sodium ions, ammonium ions and potassium ions; and outputting information on the measured concentration of the ions in the dampening water;

a dampening water temperature measuring means capable of measuring the temperature of said dampening water and outputting information on the measured temperature;

an ion concentration information correcting means capable of correcting the information on the measured concentration of the ions in the dampening water, in accordance with the information on the measured temperature of the dampening water; and an etching solution concentration adjusting means capable of adjusting the concentration of the etching solution in the dampening water, in accordance with the corrected information on the ion concentration.

DESCRIPTION OF THE PREFERRED EMBODIMENTS

Figure 1:
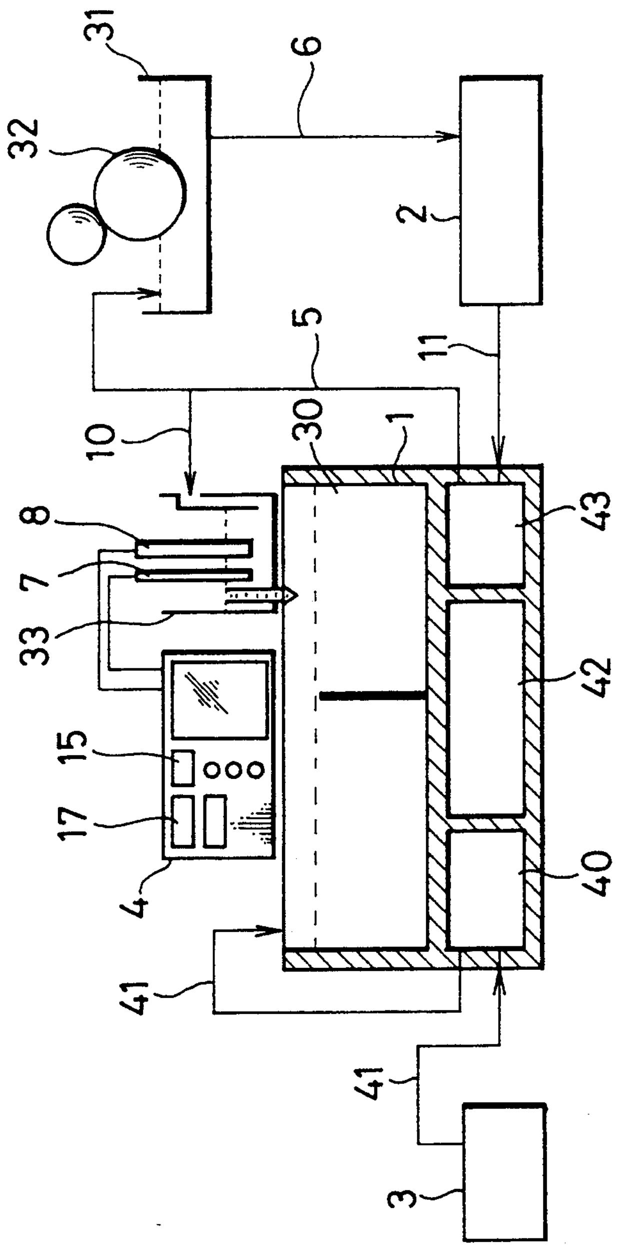
FIG. 1 schematically illustrates the construction of a dampening water controller according to Example 1 of the present invention.

The dampening water controller of the present invention will first be generically described below.

The dampening water controller of the present invention basically has an ion concentration measuring means capable of measuring the concentration of specific anions or cations contained in an etching solution in dampening water, and outputting information on the measured concentration of the ions in the dampening water; a dampening water temperature measuring means capable of measuring the temperature of the dampening water and outputting information on the measured temperature; an ion concentration information correcting means capable of correcting the information on the measured concentration of the ions in the dampening water, in accordance with the information on the measured temperature of the dampening water; and an etching solution concentration adjusting means capable of adjusting the concentration of the etching solution in the dampening water, in accordance with the corrected information on the ion concentration.

More specifically, the dampening water controller of the present invention, which takes note of specific ions (herein also called "object ions") in dampening water, is provided with means for well precisely detecting the concentration of object ions in the dampening water, judging whether or not the concentration of an etching solution is in a proper state, and, if not, making adjustment so that it is brought into a proper state. Also taking account of the fact that measured data are variable depending on changes in temperature of the dampening water serving as a sample for examination, the controller of the present invention is also provided with mean for correcting the measured data in accordance with information on dampening water temperature monitored at the same time during the use of the dampening water, to better precisely determine the concentration of object ions, and for making the above judgement and adjustment.

The construction in which the concentration of etching solution in the dampening water is directly adjusted in accordance with the corrected information on the ion concentration, the dampening water controller of the present invention may be replaced with the construction in which a means for converting the corrected information on the concentration of object ions into information on the concentration of etching solution in the dampening water is added so that the concentration of etching solution in the dampening water is adjusted in accordance with the information on the concentration of the etching solution. In this embodiment, a means for displaying the information on the concentration of the etching solution may also be added.

The object ions are not ions originating from water, impurities, a pH adjuster, etc., but ions contained in only the etching solution. Among ions preferable as the object ions, ions contained in the largest quantity and on which ion concentration can be readily determined are exemplified by nitrate ions ($NO_3^-$). When it is intended to more improve the precision or to use a special etching solution, object ions that may be used in place of the nitrate ions or may be used in combination in addition to the nitrate ions may include anions appropriately selected from nitrite ions ($NO_2^-$), phosphate ions ($PO_4^{3-}$), fluoride ions ($F^-$), sulfate ions ($SO_4^{2-}$) and sulfide ions ($S^{2-}$) and cations appropriately selected from sodium ions ($Na^{30}$), ammonium ions ($NH_4^+$) and potassium ions ($K^+$).

As a means for determining the concentration of the specific ions, it may be either a direct means or a indirect means. For example, the indirect means may include what is called the ion-selective electrode method (JIS K0122). According to this ion-selective electrode method, a given ion-selective electrode responds to the object ions to be measured, in a measuring system of "reference electrode/solution to be examined/ion-selective electrode", and produces a potential difference corresponding to ionic activities according to the Nernst equation. In respect of ionic activity a, a given relationship is established between coefficient of activity $\gamma$ and ion concentration m, i.e., $a=\gamma \cdot m$. Therefore, if the coefficient of activity is known, it becomes possible to directly calculate ion concentration on the basis of the potential difference.

When the above ion-selective electrode method is applied, an impurity separation means may be added to the system so that the lifetime of the electrode can be elongated, which is a means for removing impurities brought into the dampening water and feeding the resulting impurities-free water to the zone corresponding to the ion concentration measuring means. A cation separation means may also be added to the system so that electrodes can be prevented from deteriorating with occurrence of deposits on the surface of the electrode on the cathode side, which is a means for separating only cations from the dampening water serving as a sample for examination, and feeding the resulting cations-free dampening water to the zone corresponding to the ion concentration measuring means.

The dampening water controller according to the present invention can also bring about desirable results also when used in combination with a dampening water controller different from the present invention, e.g., a dampening water controller in which the alcohol concentration previously described in relation to the prior art is monitored and its concentration is controlled.

According to the dampening water controller of the present invention, the concentration of at least one kind of ions selected from the specific anions and cations contained in only the etching solution of the dampening water circulatively used is measured, and the concentration of etching solution in the dampening water is controlled in accordance with the information on this ion concentration. This makes it possible to control the concentration of etching solution in the dampening water in a higher precision than that in conventional methods relying on the pH values or conductivity of dampening water.

The dampening water controller of the present invention will be described below in detail by giving Examples.

EXAMPLE 1

A dampening water controller according to an example in which nitrate ions are selected as the object ions will be described below with reference to the accompanying drawings.

As shown in FIG. 1, this dampening water controller comprises a monitoring tank 33 in which dampening water 30 fed from a dampening water tank 1 is stored, a nitrate ion concentration sensor 8 and a dampening water temperature sensor 7 which are provided in the monitoring tank 33, and a control means 4 into which information from each sensor is inputted to make control of the dampening water. These constitute the main part of the dampening water controlled.

First, as shown in FIG. 1, the dampening water 30 stored in the dampening water tank 1 is sent to a water fountain 31 provided therein with a water fountain roller 32, through a water feed pipe 5 by means of a circulating pump 43, where it is led to rollers of a printer. The water fountain 31 is so designed for the dampening water 30 to be kept in a given liquid quantity. The dampening water 30 having been not consumed in the printer is circulated into the dampening water tank 1 through a water return pipe 6, a dampening water subtank 2, a subtank discharge pipe 11, the circulation pump 43 and a cooler 42. The dampening water 30 is circulated in this way, and hence ink and paper dust or fine fragments of printing paper are brought into it as impurities as previously stated.

A stock solution of the etching solution is stored in an etching solution reservoir 3. The etching solution is fed into the dampening water tank 1 in an appropriate quantity from the etching solution reservoir 3 through an etching solution feed pipe 41 by means of an etching solution feed pump 40.

The above monitoring tank 33 is so constructed that the dampening water 30 is fed into it through a water feed branch pipe 10 partly branched from the water feed pipe 5 and also its water level can be always kept constant.

In the dampening water 30 stored in the monitoring tank 33, a nitrate ion concentration sensor 8 comprised of a liquid membrane type ion-selective electrode and a reference electrode is immersed as an etching solution concentration measuring means, and also a dampening water temperature sensor 7 is immersed as the dampening water temperature measuring means that measures the temperature of the dampening water 30.

The nitrate ion concentration sensor 8 measures the concentration of nitrate ions in the dampening water 30 to which the etching solution has been added, utilizing as a basis an electromotive force produced across the electrodes, and outputs information on the etching solution concentration to the control means 4. The dampening water temperature sensor 7 measures the temperature of the dampening water 30 and outputs temperature information for correcting the information on the nitrate ion concentration, to the control means 4.

Figure 2:
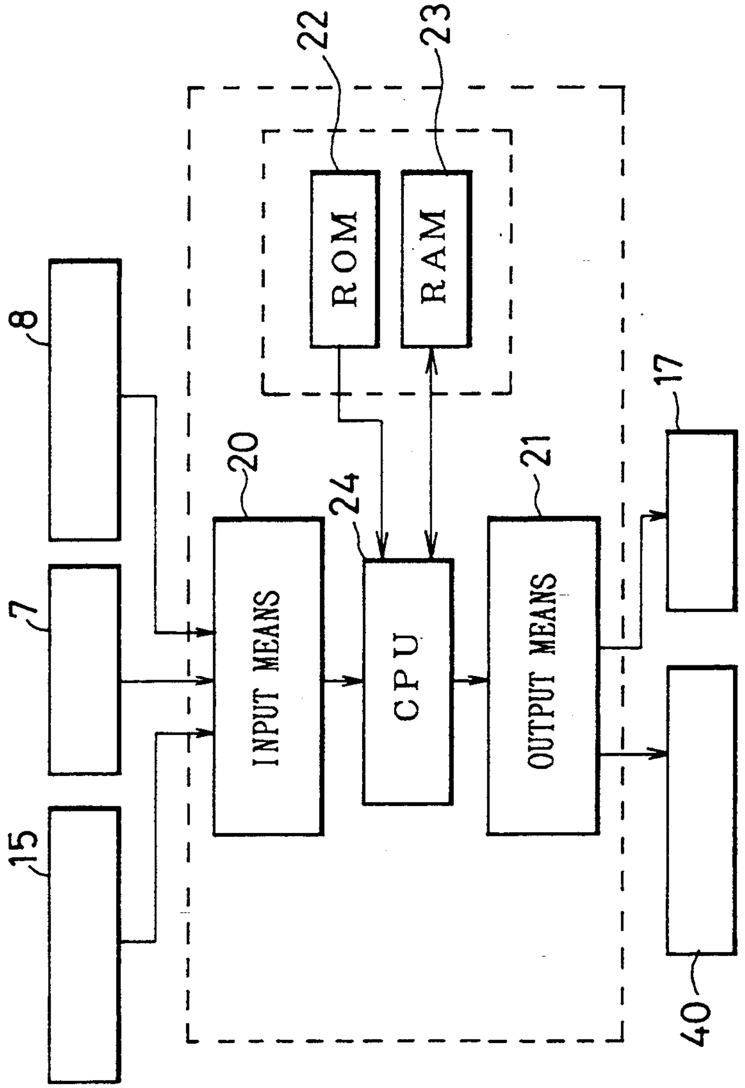
FIG.2 is a block diagram to show control means of the dampening water controller according to Example 1.
Figure 3:
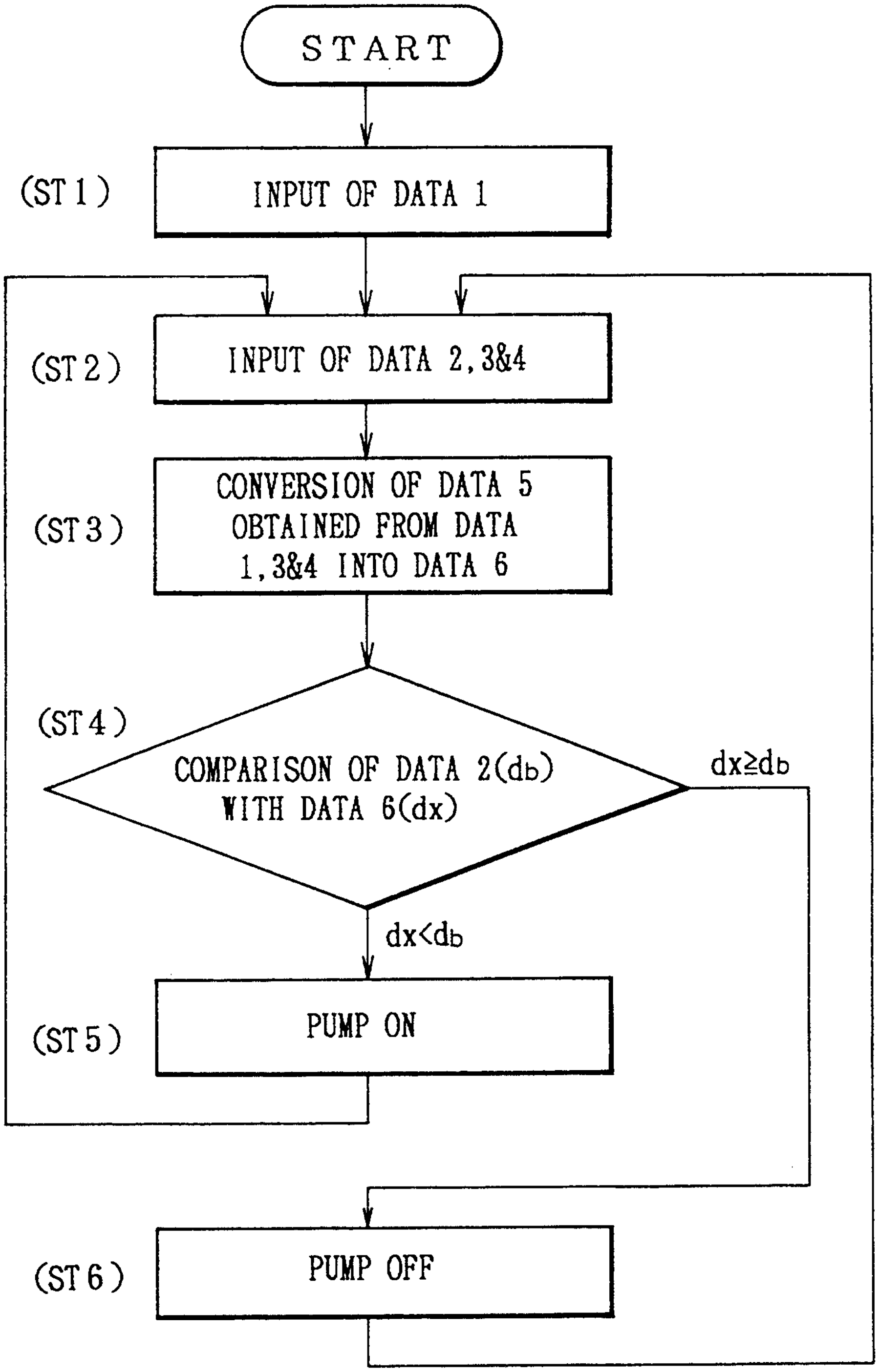
FIG. 3 is a flow chart to show operating steps of the dampening water controller according to Example 1.

The above control means 4 is constituted of a microcomputer system as shown in FIG. 2, whose main part is comprised of an input means 20, a CPU 24 that controls the whole system, a RAM 23 into and from which data are written and read from the CPU 24, and ROM 22 having been programmed with instructions as shown in FIG. 3 in the form of a flow chart, and an output means 21.

In the ROM 22, in addition to the above program, correction data based on a characteristic diagram showing the relationship between the concentration of nitrate ions contained in the dampening water 30 and the temperature of the dampening water 30, and the relationship between the nitrate ion concentration and the etching solution concentration are stored in the form of a table. These correction data are obtained from measured data set previously.

To the RAM 23, calibration information on the nitrate ion concentration (DATA 1), a value set on an external switch 15 for setting the etching solution concentration (DATA 2), which is a threshold value used as a standard concentration $d_b$ on the basis of which the concentration of etching solution in the dampening water 30 is controlled, are inputted through the input means 20. Information on the ion concentration in the dampening water 30 (DATA 3) and information on the temperature of the dampening water 30 (DATA 4) are also temporarily stored in it (see ST1 to AT 2 in FIG. 3). The calibration information on the nitrate ion concentration is meant to be information obtained in order to previously ascertain the response, etc. of the ion-selective electrode, by measuring ion concentrations of calibration solutions having a predetermined etching solution concentration (e.g., a calibration solution with an etching solution concentration of 3% and a calibration solution with an etching solution concentration of 0% are used) before the concentration of nitrate ions contained in the etching solution in the dampening water 30 serving as a sample for examination is measured, as in commonly available measuring apparatus in various fields.

In the CPU 24, the operation as shown below is carried out on the bases of the information stored in the RAM 23 and the information stored in the ROM 22.

First, the CPU 24 calibrates the information on the actually measured nitrate ion concentration in the dampening water 30 (DATA 3) in accordance with the calibration information on the nitrate ion concentration (DATA 1). It also corrects variations in the nitrate ion concentration on the dampening water 30 in accordance with the information on the temperature of the dampening water 30 (DATA 4). Thus, a corrected nitrate ion concentration of the dampening water 30 (DATA 5) is obtained. The CPU 24 converts the corrected nitrate ion concentration of the dampening water 30 (DATA 5) into an etching solution concentration $d_x$ and handles it as information on the etching solution concentration (DATA 6) (see ST3 in Fig. 3).

Next, the CPU 24 compares the etching solution concentration $d_x$ with the standard concentration $d_b$ having been set and inputted through the etching solution concentration setting switch 15 to judge their relationship of high-low fluctuation (see ST4 in FIG. 3). The output means 21 outputs signals for PUMP ON or PUMP OFF to the etching solution feed pump 40 in accordance with the results of the judgment.

In the case when the etching solution concentration $d_x$ in the dampening water 30 is lower than the standard concentration $d_b$ used for control, the etching solution feed pump 40 is driven (see ST5 in FIG. 3) and the stock solution of the etching solution is fed into the dampening water tank 1, so that the quantity of the etching solution contained in the dampening water 30 increases.

In the case when the etching solution concentration $d_x$ in the dampening water 30 is equal to the standard concentration $d_b$ used for control, the etching solution feed pump 40 is stopped (see ST6 in FIG. 3) and the stock solution of the etching solution is stopped being fed into the dampening water tank 1. Usually, there may occur no instance in which the etching solution concentration $d_x$ in the dampening water 30 becomes higher than the standard concentration $d_b$ used for control. If, however, this has occurred, the system is so set up as to make an alarm signal from an alarm system (not shown) to give attention to an operator.

In the course of the operation of the printer, a consumed etching solution is compensated while continually repeating this control process, so that the etching solution concentration in the dampening water 30 is made close to the standard concentration used for control and the etching solution concentration in the dampening water 30 is substantially kept constant.

Corrected values of the etching solution concentration in the dampening water 30 and the information on the temperature of the dampening water 30 are digitally displayed on a display device 17. The present apparatus automatically repeats the processing described above. Here, to stop the apparatus, though not clearly shown in the above flow chart, an operator can stop it at arbitrary timing by, for example, operating a stop switch or giving a stop command.

EXAMPLE 2

Figure 4:
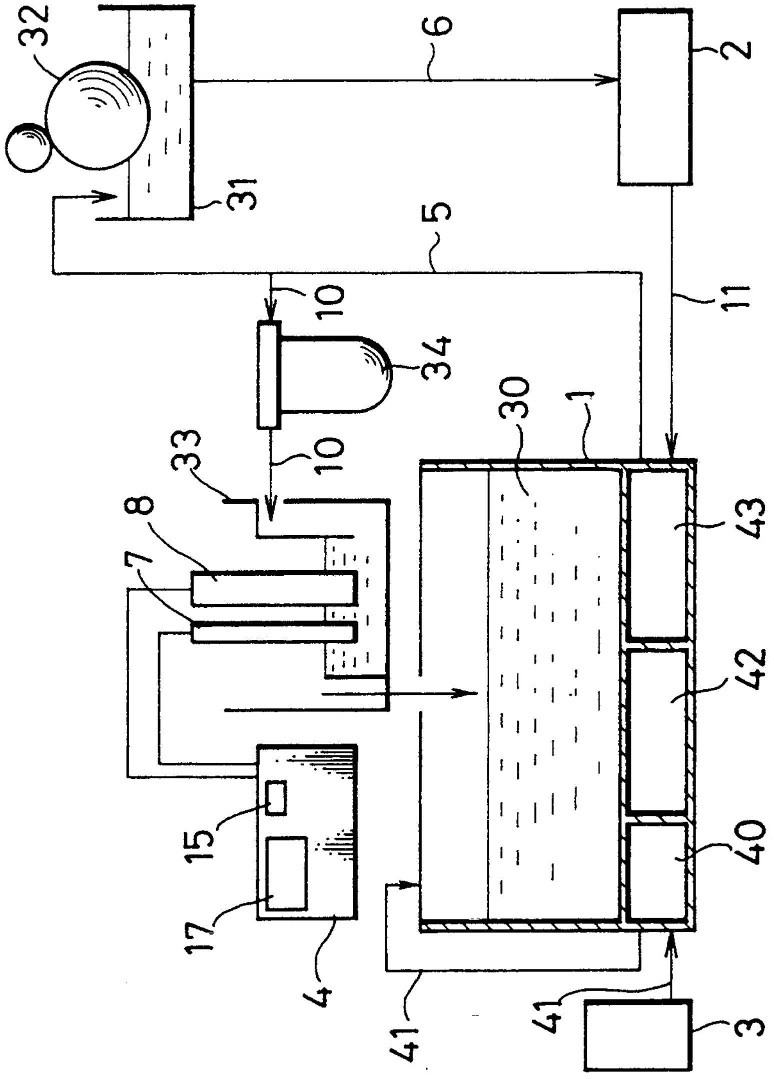
FIG. 4 schematically illustrates the construction of a dampening water controller according to Example 2 of the present invention.

The dampening water controller according to this Example is substantially the same as the dampening water controller according to Example 1 except that, as shown in FIG. 4, a filter 34 serving as the impurity separation means is provided in the course of the water feed branch pipe 10.

More specifically, the dampening water 30 is fed through the water feed branch pipe 10. This apparatus is so designed that impurities such as ink and paper dust are separated from the dampening water 30 by the action of this filter 34 and the resulting impurities-free dampening water 30 is sent to the monitoring tank 33. The filter 34 used in this apparatus is WIND CARTRIDGE CS (trade name; available from Nihon Filter Co., Ltd.) having a pore size of about 50 μm to about 100 μm. The dampening water 30 having been monitored is returned to the dampening water tank 1 through the monitoring tank 33.

Figure 5:
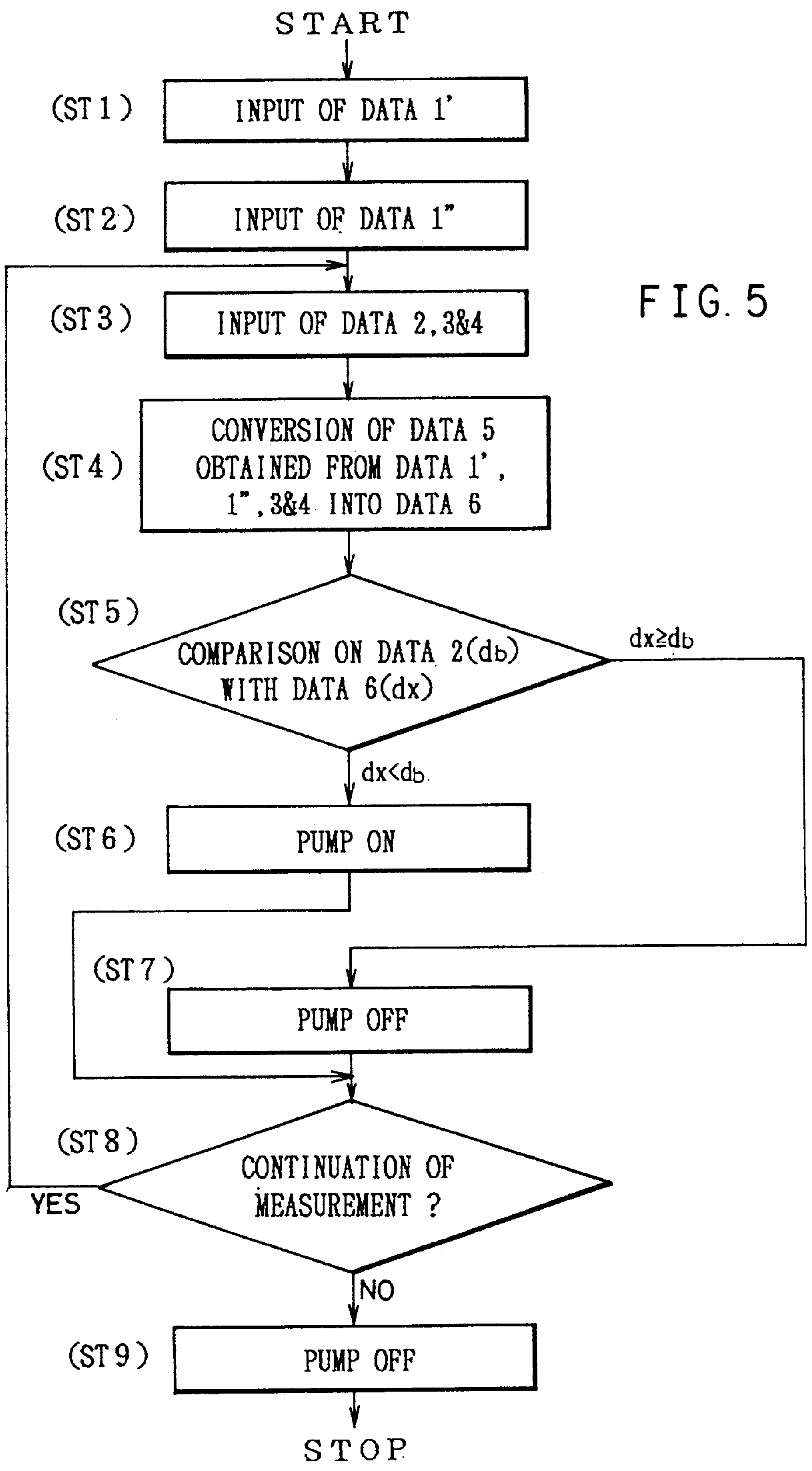
FIG. 5 is a flow chart to show operating steps of the dampening water controller according to Example 2.

The ROM 22 that constitutes part of the control means 4 (see FIG. 2) of this apparatus has been programmed with instructions as represented by a flow chart (see FIG. 5) more detailed than that in FIG. 3. More specifically, in this apparatus, like the dampening water according to Example 1, a calibration value obtained from a calibration solution (i) (city water) with an etching solution concentration of 0% (DATA 1') is measured by means of the nitrate ion concentration sensor 8 comprised of an ion-selective electrode and a reference electrode and is stored in the memory (see ST1 in FIG. 5), and at the same time a calibration value obtained from a calibration solution (ii) (city water) with an etching solution concentration of 3% (DATA 1") is similarly measured by means of the nitrate ion concentration sensor 8 and is stored in the memory (see ST2 in FIG. 5), where a linear approximate value between two points in two-point calibration is calculated to determine the calibration information on the nitrate ion concentration (DATA 1). At the time of this calibration, corrections are also made according to the temperature of the calibration solutions. In the flow chart of FIG. 5, the stop of the apparatus, whose illustration is omitted in the flow chart of FIG. 3, is especially specified (see ST8 to ST9 in FIG. 5). That is, this apparatus automatically repeatedly carries out the processing described in Example 1 as long as the operator does not stop the apparatus by operating a stop switch or giving a stop command (not shown). The operator can stop the apparatus at arbitrary timing.

In the dampening water controller according to this Example, no impurities such as ink and paper dust are included in the dampening water 30 sent to the monitoring tank 33 and hence it becomes possible to elongate the lifetime of the ion-selective electrode, etc. compared with the dampening water controller according to Example 1, bringing about the advantage that the maintenance of the apparatus can be made easier.

EXAMPLE 3

Figure 6:
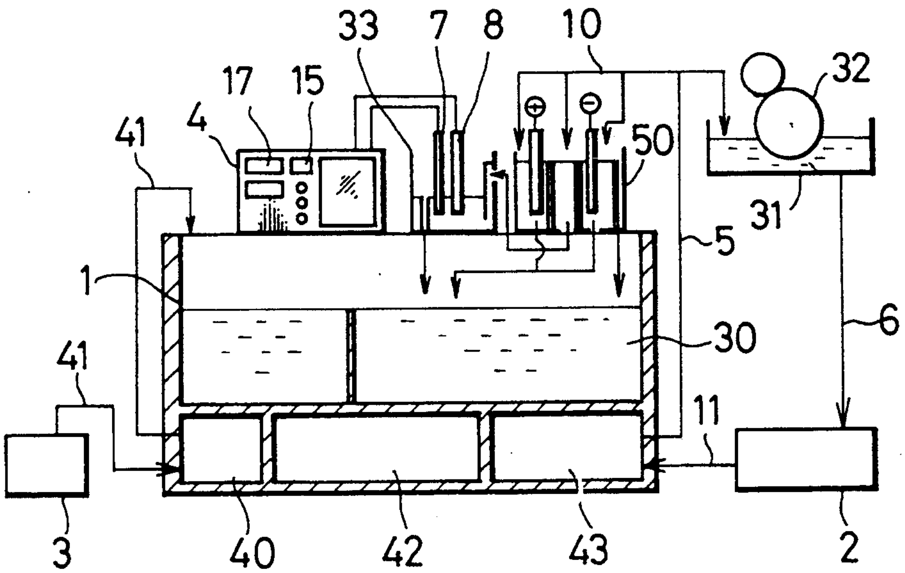
FIG. 6 schematically illustrates the construction of a dampening water controller according to Example 3 of the present invention FIG. 7 schematically illustrates a part of FIG. 6 in more detail.

The dampening water controller according to this Example is substantially the same as the dampening water controller according to Example 1 except that, as shown in FIG. 6, an ion separation chamber 50 is provided between the water feed pipe 5 and the monitoring tank 33.

Figure 7:
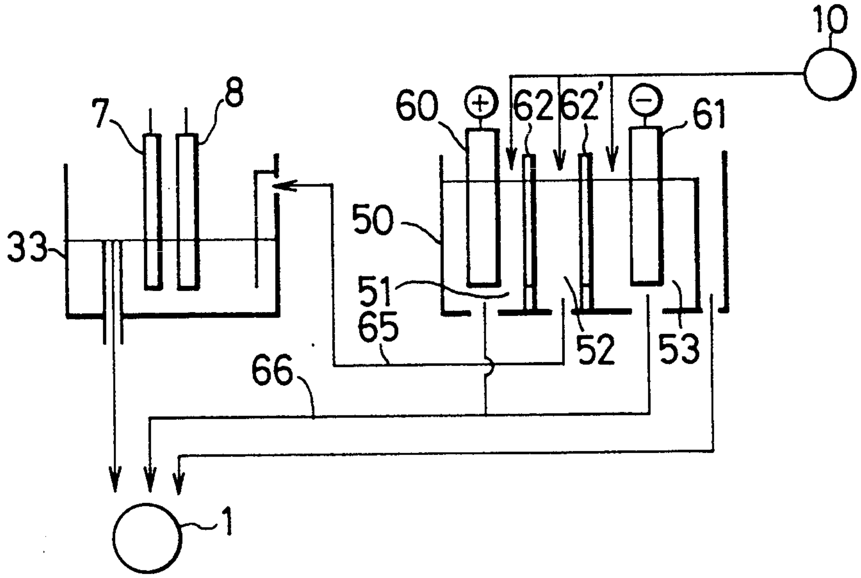
Figure 8:
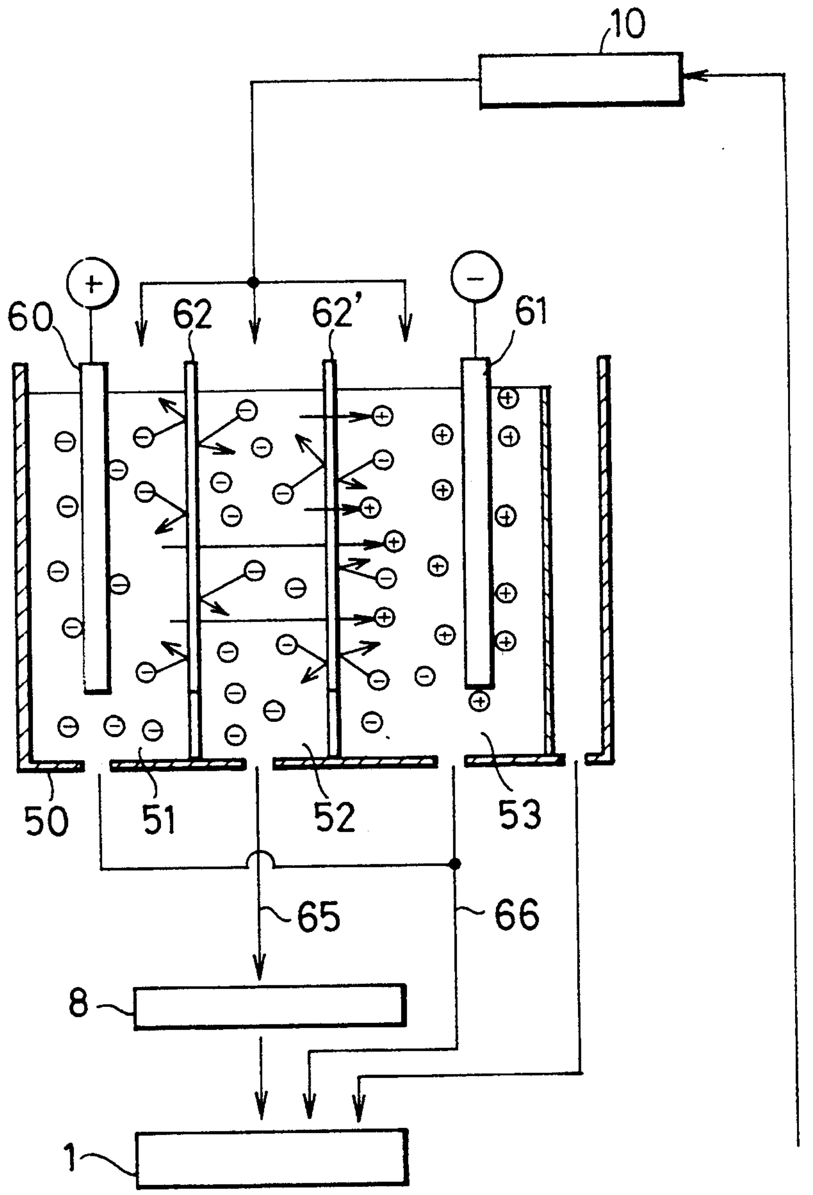
FIG. 8 schematically illustrates an ion separation chamber of the dampening water controller according to Example 3.

More specifically, the ion separation chamber 50 comprises, as shown in FIGS. 7 to 8, a cation-selective electrode chamber 51 partitioned with two cation-exchange membranes 62 and 62' (trade name: SELEMION; cation-exchange membranes available from Asahi Glass Co., Ltd.), a dampening water anionic solution chamber 52 and an anion-selective electrode chamber 53. These constitute the main part of the ion separation chamber. An anode plate 60 is also provided in the cation-selective electrode chamber 51, and an cathode plate 61 in the anion-selective electrode 53. The dampening water 30 serving as a sample for examination is fed into each of these cation-selective electrode chamber 51, dampening water anionic solution chamber 52 and anion-selective electrode chamber 53 through the water feed branch pipe 10. With regard to the dampening water 30 fed into the dampening water anionic solution chamber 52, the cations in the dampening water 30 pass through the cation-exchange membrane 62', attracted to the cathode plate 61 of the anion-selective electrode chamber 53, and removed from the chamber 52. On the other hand, the anions in the dampening water 30 are attracted to the anode plate 60 of the cation-selective electrode chamber 51, but can not pass through the cation-exchange membrane 62, and hence the dampening water 30 from which only cations have been removed remains in the chamber 52. With regard to the dampening water 30 fed into the cation-selective electrode chamber 51, its anions are attracted to the anode plate 60, but on the other hand the cations in the dampening water 30 are repelled therefrom and some of them pass through the cation-exchange membranes 62 and 62' and are attracted to the cathode plate 61 of the anion-selective electrode chamber 53. With regard to the dampening water 30 fed into the anion-selective electrode chamber 53, its cations are attracted to the cathode plate 61 and its anions can not pass through the cation-exchange membrane 62' to remain in the anion-selective electrode chamber 53.

Thus, only the dampening water 30 in the dampening water anionic solution chamber 52 is fed into the monitoring tank 33 through a dampening water anionic solution feed pipe 65, and the nitrate ion concentration in the dampening water 30 fed thereinto is measured by the nitrate ion concentration sensor 8. The dampening water 30 held in the cation-selective electrode chamber 51 and anion-selective electrode chamber 53 is again returned to the dampening water tank 1 through an ionic solution return pipe 66, and the dampening water 30 having been monitored is also returned to the dampening water tank 1 through the monitoring tank 33.

In the dampening water controller according to this Example, no cations are contained in the dampening water 30 fed into the monitoring tank 33, and hence it becomes possible to elongate the lifetime of the ion-selective electrodes, etc. compared with the dampening water controller according to Example 1, bringing about the advantage that the maintenance of the apparatus can be made easier. In other words, if the ion-selective electrode method is carried out without such treatment, unnecessary deposits may be formed on the surface of the electrode plate on the cathode side, tending to result in a short lifetime of the electrode plate and cause a little difficulty in the performance and stability of measurement. On the other hand, providing the chamber in which the cations that may cause the deposits (which, though not accurately specified, are considered to be concerned with cations since the deposition occurs on the cathode side) are separated from the dampening water 30 makes it possible to elongate the lifetime of the ion-selective electrodes, etc. and make the maintenance of the apparatus easier.

EXAMPLE 4

Figure 9:
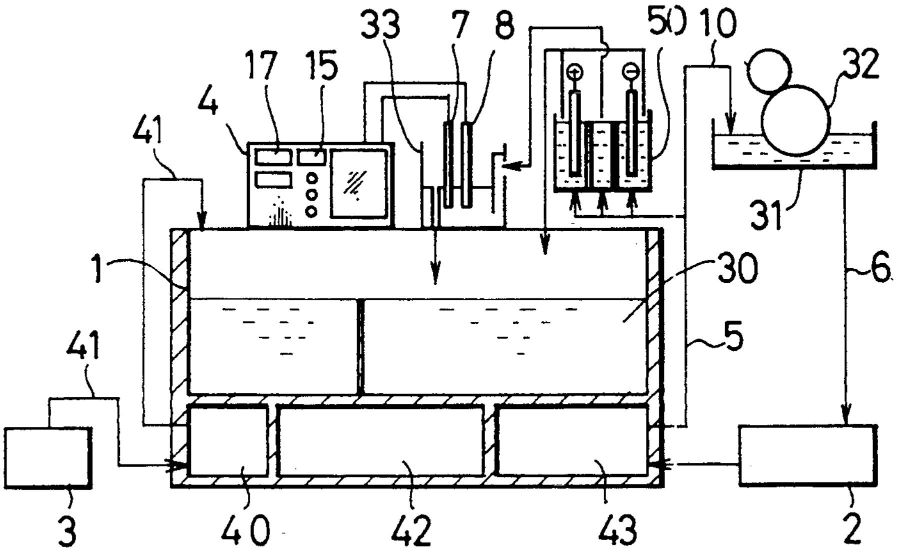
FIG. 9 schematically illustrates the construction of a dampening water controller according to Example 4 of the present invention.
Figure 10:
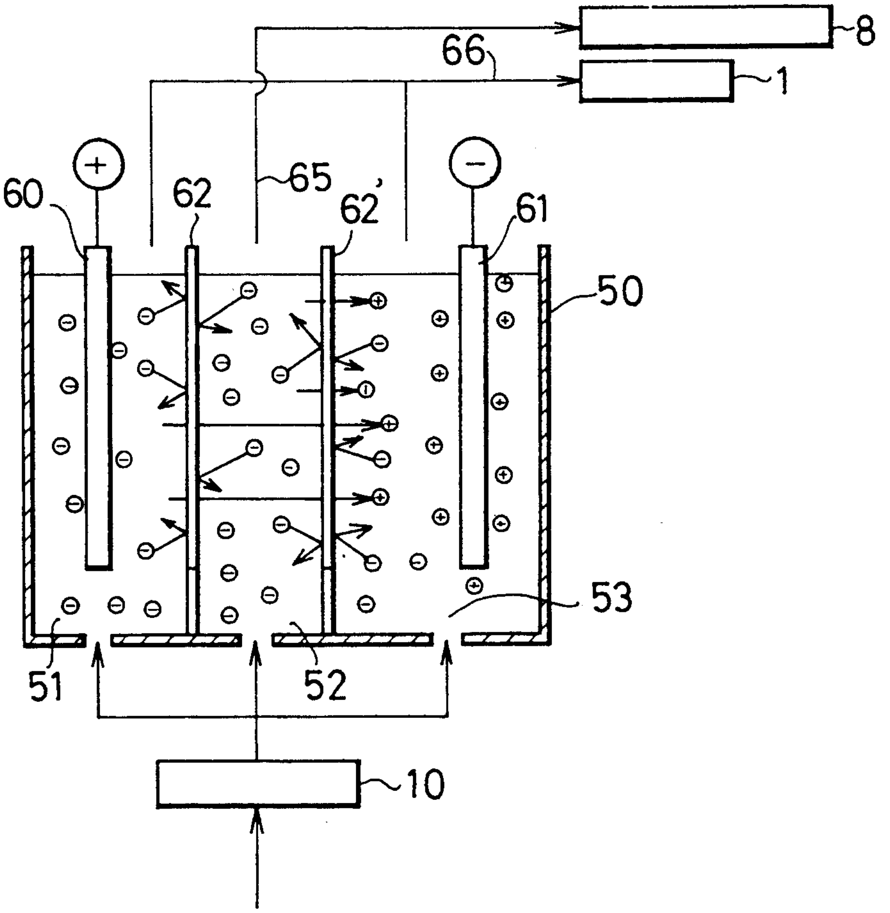
FIG. 10 schematically illustrates an ion separation chamber of the dampening water controller according to Example 4.

The dampening water controller according to this Example is substantially the same as the dampening water controller according to Example 3 except that, as shown in FIGS. 9 and 10, the dampening water 30 is fed into the ion separation chamber 50 from its bottom side and also the dampening water 30 from which cations have been removed is fed into the monitoring tank 33 from the top side of the chamber.

In the dampening water controller according to this Example also, no cations are contained in the dampening water 30 fed into the monitoring tank 33, and hence it becomes possible to elongate the lifetime of the ion-selective electrodes, etc. compared with the dampening water controller according to Example 1, bringing about the advantage that the maintenance of the apparatus can be made easier.

EXAMPLE 5

Figure 11:
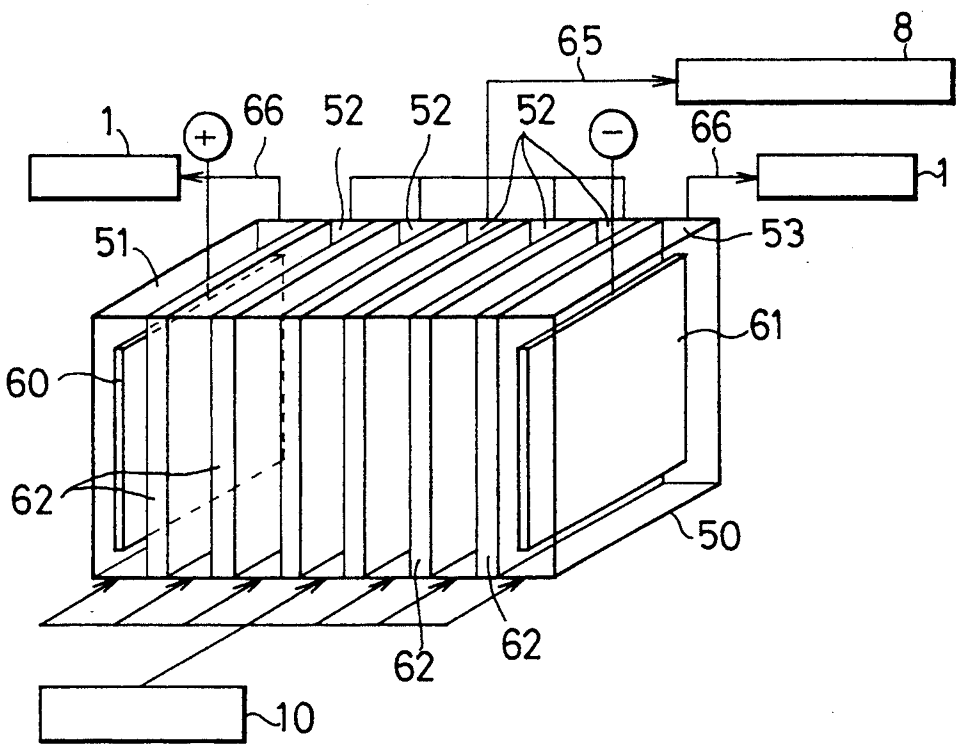
FIG. 11 schematically illustrates an ion separation chamber of the dampening water controller according to Example 5.

The dampening water controller according to this Example is substantially the same as the dampening water controller according to Example 3 except that, as shown in FIG. 11, the ion separation chamber 50 is mainly comprised of a cation-selective electrode chamber 51 partitioned with a plurality of cation-exchange membranes (trade name: NEOSEPTA; cation-exchange membranes available from Tokuyama Soda Co., Ltd.) 62, a plurality of dampening water anionic solution chambers 52 and an anion-selective electrode chamber 53, the dampening water 30 is fed into the ion separation chamber 50 from its bottom side, and also the dampening water 30 from which cations have been removed is fed into the monitoring tank 33 from the top side of the chamber through a dampening water anionic solution feed pipe 65.

In the dampening water controller according to this Example also, no cations are contained in the dampening water 30 fed into the monitoring tank 33, and hence it becomes possible to elongate the lifetime of the ion-selective electrodes, etc. compared with the dampening water controller according to Example 1, bringing about the advantage that the maintenance of the apparatus can be made easier. In addition, since the ion separation chamber 50 is provided with a plurality of dampening water anionic solution chamber 52, the cations in the dampening water can be separated in a shorter time and in a larger quantity.

EXAMPLE 6

Figure 12:
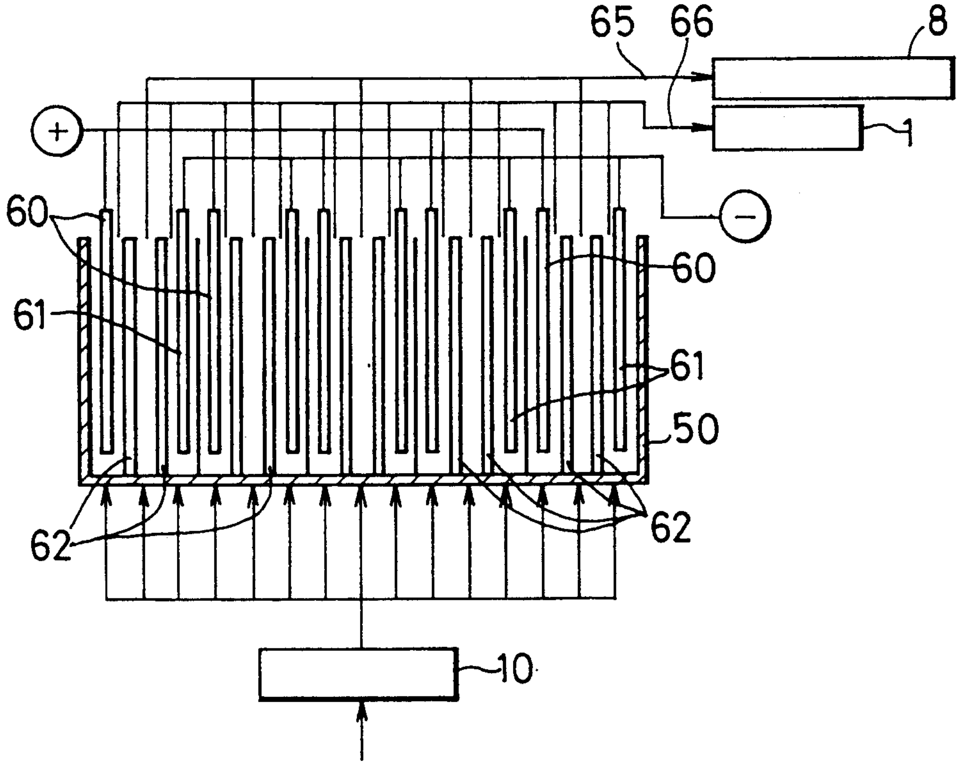
FIG. 12 schematically illustrates an ion separation chamber of the dampening water controller according to Example 6.

The dampening water controller according to this Example is substantially the same as the dampening water controller according to Example 3 except that, as shown in FIG. 12, the ion separation chamber 50 is comprised of a group of ion separation chambers each comprising a cation-selective electrode chamber 51 partitioned with two cation-exchange membranes 62 and 62, a dampening water anionic solution chamber 52 and an anion-selective electrode chamber 53, the dampening water is fed into the ion separation chamber 50 from its bottom side, and also the dampening water from which cations have been removed is fed into the monitoring tank from the top side of the chamber through a dampening water anionic solution feed pipe 65. An anode plate 60 is provided in each cation-selective electrode chamber 51, and a cathode plate 61 in each anion-selective electrode chamber 53.

In the dampening water controller according to this Example also, no cations are contained in the dampening water 30 fed into the monitoring tank 33, and hence it becomes possible to elongate the lifetime of the ion-selective electrodes, etc. compared with the dampening water controller according to Example 1, bringing about the advantage that the maintenance of the apparatus can be made easier. In addition, since the ion separation chamber 50 is comprised of a plurality of ion separation chambers, the cations in the dampening water can be separated in a shorter time and in a larger quantity than in the dampening water controller according to Example 5.

As having been described above, the dampening water controller of the present invention comprises an ion concentration measuring means capable of measuring the concentration of at least one kind of ions (object ions) selected from specific anions or cations contained only in an etching solution in dampening water, and outputting information on the measured concentration of the ions in the dampening water; a dampening water temperature measuring means capable of measuring the temperature of the dampening water and outputting information on the measured temperature; an ion concentration information correcting means capable of correcting the information on the measured concentration of the ions in the dampening water, in accordance with the information on the measured temperature of the dampening water; and an etching solution concentration adjusting means capable of adjusting the concentration of the etching solution in the dampening water, in accordance with the corrected information on the ion concentration. Hence, compared with conventional dampening water controllers that control the dampening water in accordance with the pH values or conductivity of dampening water, the present dampening water controller can have less influence from the impurities such as ink and paper dust brought into the dampening water, and can control the concentration of the etching solution in a much higher precision.

Thus, the present invention is effective for producing high-quality offset prints in a large quantity and with ease.

What is claimed is:

1. A dampening water controller for controlling the concentration of an etching solution in dampening water circulatively used in offset printing, said controller comprising;

an ion concentration measuring means for measuring the concentration of anions or cations contained in the etching solution in said dampening water; said anions being selected from the group consisting of nitrate ions, nitrite ions, phosphate ions, fluoride ions, sulfate ions and sulfide ions and said cations being selected from the group consisting of sodium ions, ammonium ions and potassium ions; and outputting information on the concentration of the ions in the dampening water after the measuring by said ion concentration measuring means;

a dampening water temperature measuring means for measuring a temperature of dampening water and outputting information on the temperature after the measuring by said dampening water temperature measuring means;

an ion concentration information correcting means for correcting said information measured by said ion concentration measuring means, in accordance with the information measured by said dampening water temperature measuring means; and an etching solution concentration adjusting means for adjusting the concentration of the etching solution in the dampening water, in accordance with the information corrected by the ion concentration information correcting means.

2. A dampening water controller for controlling the concentration of an etching solution in dampening water circulatively used in offset printing, said controller comprising;

an ion concentration measuring means for measuring the concentration of anions or cations contained in the etching solution in said dampening water; said anions being selected from the group consisting of nitrate ions, nitrite ions, phosphate ions, fluoride ions, sulfate ions and sulfide ions and said cations being selected from the group consisting of sodium ions, ammonium ions and potassium ions; and outputting information on the concentration of the ions in the dampening water after the measuring by said ion concentration measuring means;

a dampening water temperature measuring means for measuring a temperature of dampening water and outputting information on the temperature after the measuring by said dampening water temperature measuring means;

an ion concentration information correcting means for correcting the information measured by said ion concentration measuring means, in accordance with the information measured by said dampening water temperature measuring means;

an etching solution concentration information conversion means for converting the information corrected by the ion concentration information correcting means into information on the concentration of etching solution in the dampening water and outputting the information on the concentration of the etching solution; and an etching solution concentration adjusting means for adjusting the concentration of the etching solution in the dampening water, in accordance with the information on the concentration of the etching solution.

3. The dampening water controller according to claim 2, wherein said etching solution concentration information conversion means is provided with a display means for displaying the information on the concentration of the etching solution.

4. The dampening water controller according to claim 1, wherein said ion concentration measuring means comprises an ion-selective electrode and a reference electrode.

5. The dampening water controller according to claim 2, wherein said ion concentration measuring means comprises the an ion-selective electrode and a reference electrode.

6. The dampening water controller according to claim 1, which is provided with an impurity separation means for removing impurities brought into the dampening water serving as a sample for examination, and feeding a resulting water free of impurities to a zone corresponding to the ion concentration measuring means.

7. The dampening water controller according to claim 2, which is provided with an impurity separation means for removing impurities brought into the dampening water serving as a sample for examination, and feeding a resulting water free of impurities to a zone corresponding to the ion concentration measuring means.

8. The dampening water controller according to claim 1, which is provided with a cation separation means for separating only cations from the dampening water serving as a sample for examination, and feeding a resulting dampening water free of cations to a zone corresponding to the ion concentration measuring means.

9. The dampening water controller according to claim 2, which is provided with a cation separation means for separating only cations from the dampening water serving as a sample for examination, and feeding a resulting dampening water free of cations to a zone corresponding to the ion concentration measuring means.

10. The dampening water controller according to claim 1, wherein the ions measured by said ion concentration measuring means are nitrate ions contained in the etching solution in the dampening water.

11. The dampening water controller according to claim 2, wherein the ions measured by said ion concentration measuring means are nitrate ions contained in the etching solution in said dampening water.

12. The dampening water controller according to claim 1, wherein the ions measured by said ion concentration measuring means are nitrite ions contained in the etching solution in said dampening water.

13. The dampening water controller according to claim 2, wherein the ions measured by said ion concentration measuring means are nitrite ions contained in the etching solution in said dampening water.

14. The dampening water controller according to claim 1, wherein the ions measured by said ion concentration measuring means are phosphate ions contained in the etching solution in said damping water.

15. The dampening water controller according to claim 2, wherein the ions measured by said ion concentration measuring means are phosphate ions contained in the etching solution in said dampening water.

* * * * *